(12) United States Patent
Matsumura et al.

(10) Patent No.: US 7,628,754 B2
(45) Date of Patent: Dec. 8, 2009

(54) ULTRASONOGRAPHIC DEVICE

(75) Inventors: Takeshi Matsumura, Kashiwa (JP);
Satoshi Tamano, Kashiwa (JP);
Tsuyoshi Mitake, Noda (JP); Tsuyoshi Siina, Tsukuba (JP)

(73) Assignee: Hitachi Medical Corporation, Tokyo (JP)

( * ) Notice: Subject to any disclaimer, the term of this patent is extended or adjusted under 35 U.S.C. 154(b) by 719 days.

(21) Appl. No.: 10/542,206

(22) PCT Filed: Jan. 14, 2004

(86) PCT No.: PCT/JP2004/000202

§ 371 (c)(1),
(2), (4) Date: Jul. 14, 2005

(87) PCT Pub. No.: WO2004/062503

PCT Pub. Date: Jul. 29, 2004

(65) Prior Publication Data

US 2006/0173306 A1   Aug. 3, 2006

(30) Foreign Application Priority Data

Jan. 15, 2003   (JP)   ............................... 2003-006932

(51) Int. Cl.
*A61B 8/00*   (2006.01)
(52) U.S. Cl. .................................................. 600/437
(58) Field of Classification Search ................. 600/437, 600/438, 442, 443
See application file for complete search history.

(56) References Cited

U.S. PATENT DOCUMENTS 6,558,324 B1 *  5/2003  Von Behren et al.  ........ 600/440

FOREIGN PATENT DOCUMENTS

| JP | 55-026919 A | 2/1980 |
| JP | 04-200457 A | 7/1992 |
| JP | 5-184577 | 7/1993 |
| JP | 5-317313 | 12/1993 |

(Continued)

OTHER PUBLICATIONS

Makoto Yamakawa et al., "Free hand ni Yoru Nyusen Byohen no Jitsujikan Soshiki Dansei Imaging no Kokoromi". Dai 23 Kai Choonpa Electronics no Koso to Oyo ni Kansuru Symposium, Nov. 7, 2002, pp. 297 to 298.

(Continued)

*Primary Examiner*—Long V Le
*Assistant Examiner*—Jacqueline Cheng
(74) *Attorney, Agent, or Firm*—Antonelli, Terry, Stout & Kraus, LLP.

(57) ABSTRACT

An ultrasonographic device includes an ultrasonic wave transmitter/receiver section which transmits and receives ultrasonic waves to and from a test subject through a probe, a phasing addition circuit which controls the phase of the received ultrasonic wave and generates RF signal frame data, an RF signal frame data selection section which makes variable the frame interval of the RF signal frame data to be outputted, and an elastic image generating section which sets the optimum imaging range for each elastic frame data generated based on the RF signal frame data and generates elastic image.

2 Claims, 12 Drawing Sheets

FOREIGN PATENT DOCUMENTS

| | | |
|---|---|---|
| JP | 8-66397 | 3/1996 |
| JP | 10-151131 | 6/1998 |
| JP | 2000-60853 | 2/2000 |
| JP | 2003-116855 | 4/2003 |
| JP | 2003-116855 A | 4/2003 |

OTHER PUBLICATIONS

Tsuyoshi Shiina et al., Real Time Tissue Elasticity Imaging Using the Combined Autocorrelation Method, Journal of Medical Ultrasonics, Sep. 15, 2002, vol. 29, Autumn 2002, pp. 119 to 128.

Jonathan Ophir et al., Elastography: Imaging the Elastic Properties of Soft Tissues with Ultrasound, Journal of Medical Ultrasonics, Dec. 15, 2002, vol. 29, Winter 2002, pp. 155-171.

Journal of Medical Ultrasonics, Sep. 15, 2003, vol. 30, No. 5, pp. 688 to 691.

Thomas A. Krouskop et al., "Elastic Moduli of Breast and Prostate Tissues Under Compression", Ultrasonic Imaging 20, 260-274 (1998).

* cited by examiner

ULTRASONOGRAPHIC DEVICE

TECHNICAL FIELD

The present invention relates to an ultrasonographic device by which a tomographic image of an examined part inside a test subject is obtained and displayed using ultrasonic waves, and particularly relates to an ultrasonographic device by which a distortion or an elastic modulus is calculated for each point on an image based on a group of RF signal frame data arranged in time sequence, and is displayed as an elastic image indicating the hardness or softness of living tissue in a quantitative manner.

BACKGROUND ART

A typical ultrasonographic device is conventionally constituted of an ultrasonic wave transmitter/receiver section for transmitting and receiving ultrasonic waves to and from a test subject, a tomographic scanning section for repeatedly obtaining tomographic image data in the test subject including motor tissue in a predetermined cycle by using a reflecting echo signal from the ultrasonic wave transmitter/receiver section, and an image display section for displaying time-sequence tomographic image data obtained by the tomographic scanning section. Further, the structure of living tissue in the test subject is displayed as, e.g., a B-mode image.

In relation to this device, in recent years, an external force is artificially applied from the body surface of the test subject through a pressurizer or an ultrasound probe to measure a distortion and/or elastic modulus of living tissue of an examined part, and the hardness of the tissue is displayed as an elastic image based on numeric data (elastic frame data) of a distortion or elastic modulus by using the ultrasonographic device. Such an ultrasonographic device is disclosed in JP-A-5-317313 or JP-A-2000-60853.

However, in the imaging of elastic frame data in the ultrasonographic device of the citations, a correlation operation is used between two RF signal frame data which are obtained in a series of pressuring or decompressing operations and are adjacent to each other in time sequence. Thus, when an amount of pressurization or decompression applied in a time interval between RF signal frame data constituting a group of two or more RF signal frame data does not sufficiently reach an amount of pressurization or decompression (generally about 1%) suitable for visualizing elastic image data, it is difficult to properly visualize an elastic image of elastic frame data.

During a series of pressuring or decompressing operations, when an object is diagonally and/or unevenly pressurized or decompressed, a time phase may occur in which a stress distribution in the object has a temporally irregular change. In such a time phase, a coordinate area where a stress distribution has a temporally irregular change appears in a series of elastic frame data (distortion data) in the time-base direction. Thus, an elastic image includes a temporally irregular area as noise, so that image diagnosis becomes difficult.

DISCLOSURE OF THE INVENTION

In consideration of the above-described point, it is an object of the present invention to provide an ultrasonographic device by which a difference in elasticity can be effectively visualized as an image with a high S/N ratio and a predetermined display gradation stably even in a given time phase.

An ultrasonographic device of the present invention comprises:

an ultrasound probe including an oscillator for generating ultrasonic waves, an ultrasonic wave transmitter/receiver circuit which is connected to the probe and transmits and receives the ultrasonic waves to and from a test subject, a phasing addition circuit which controls the phase of received ultrasonic waves and generates RF signal frame data, an RF signal frame data selection section which is connected to the phasing addition circuit and makes variable a frame interval of outputted RF signal frame data according to a change in pressure applied to the test subject, an elastic frame data calculation section which is connected to the RF signal frame data selection section and generates elastic frame data in time sequence based on a pair of the inputted RF signal frame data, the elastic frame data indicating a distortion or an elastic modulus of each point on a tomographic image, and an elastic image generating section which is connected to the elastic frame data calculation section and generates an elastic image based on the elastic frame data inputted from the calculation section.

Further, in the ultrasonographic device of the present invention, the elastic image generating section includes a statistical processing circuit for performing statistical processing on two or more elastic frame data corresponding to a target processing area and determines a statistical characteristic amount, a circuit for setting the upper limit value and the lower limit value of an imaging range of the elastic frame data based on the statistical characteristic amount, and a circuit for generating elastic image data from the elastic frame data while matching the upper limit value and the lower limit value with the range of a predetermined display gradation.

Other objects, features, and advantages of the present invention will become apparent from the following description of examples with reference to the accompanying drawing.

BEST MODE FOR CARRYING OUT THE INVENTION

Figure 1:
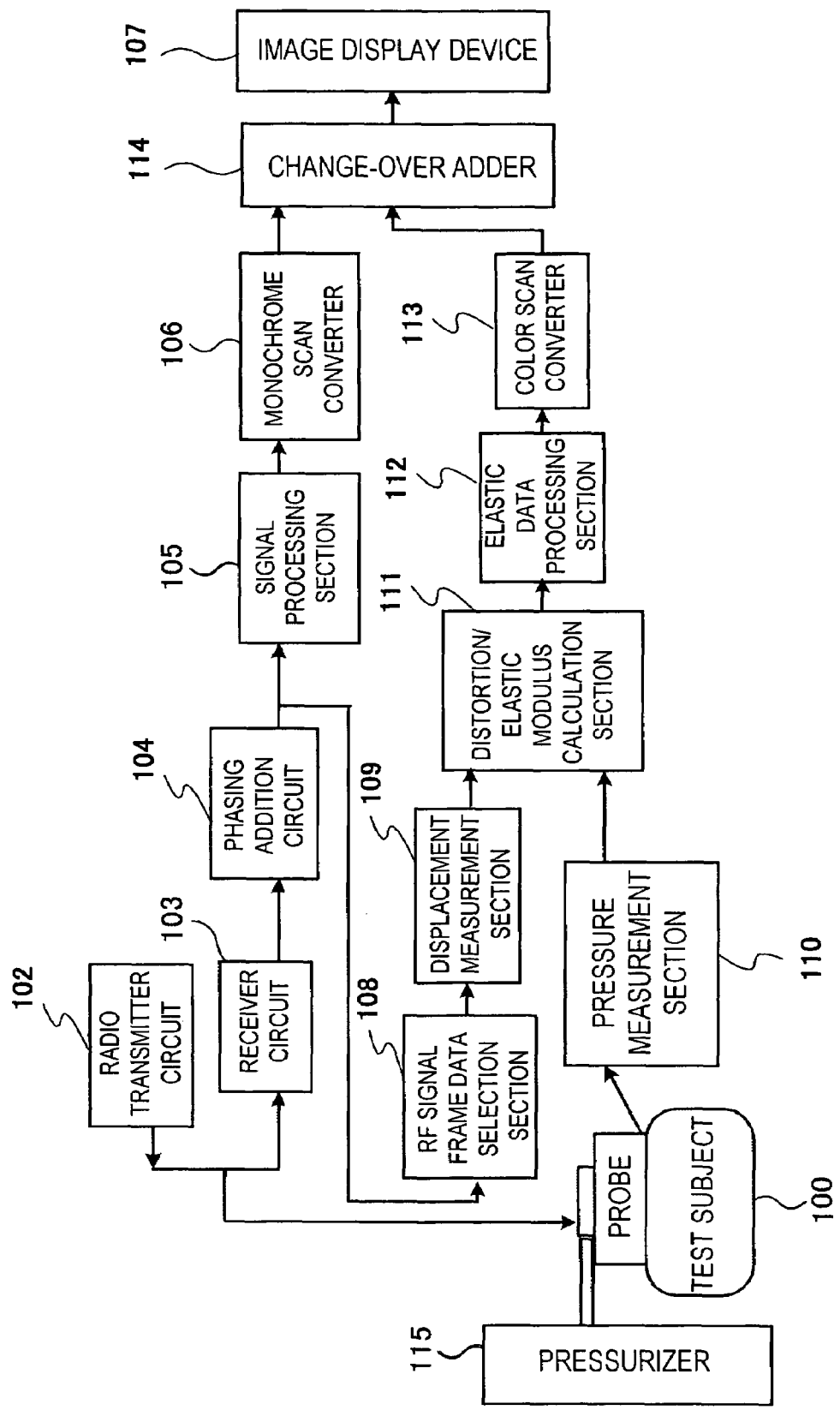
FIG. 1 is a block diagram showing an embodiment of an ultrasonographic device according to the present invention.

The following will specifically describe an embodiment of the present invention in accordance with the accompanying drawings. FIG. 1 is a block diagram showing an embodiment of an ultrasonographic device of the present invention. With the ultrasonographic device, a tomographic image of an examined part of a test subject 100 is obtained using ultrasonic waves, and an elastic image indicating the hardness or softness of living tissue can be displayed. As shown in FIG. 1, the ultrasonographic device comprises an ultrasound probe 101, a radio transmitter circuit 102, a receiver circuit 103, a phasing addition circuit 104, a signal processing section 105, a monochrome scan converter 106, an image display device 107, an RF signal frame data selection section 108, a displacement measurement section 109, a pressure measurement section 110, a distortion/elastic modulus calculation section 111, an elastic data processing section 112, a color scan converter 113, and a change-over adder 114.

The ultrasound probe 101, the radio transmitter circuit 102, the receiver circuit 103, the phasing addition circuit 104, and the signal processing section 105 constitute an ultrasonic wave transmitter/receiver section. The ultrasonic wave transmitter/receiver section causes an ultrasonic beam to scan the inside of the body of a test subject by using the ultrasound probe 101 along a fixed direction, so that a tomographic image is obtained. The ultrasound probe 101 is formed of a number of oscillators arranged like strips. The ultrasound probe 101 performs beam scanning mechanically or electronically to transmit and receive ultrasonic waves to and from a test subject. The ultrasound probe 101 includes oscillators (not shown) where ultrasonic waves are generated and reflecting echo is received. The oscillators are generally formed with the function of converting an inputted pulse wave or a transmission signal of a continuous wave into an ultrasonic wave and emitting the ultrasonic wave, and the function of receiving an ultrasonic wave reflected from the inside of the test subject, converting the ultrasonic wave into a reception signal of an electric signal, and outputting the signal.

The radio transmitter circuit 102 generates a transmission pulse for driving the ultrasound probe 101 and generating ultrasonic waves, and sets the convergent point of a transmitted ultrasonic wave at a certain depth by means of a transmission phasing addition circuit included in the radio transmitter circuit 102. The receiver circuit 103 amplifies a reflecting echo signal, which has been received by the ultrasound probe 101, with a predetermined gain. Amplified reception signals as many as the oscillators are inputted as independent reception signals to the phasing addition circuit 104. The phasing addition circuit 104 is fed with the reception signals having been amplified by the receiver circuit 103, controls the phases of the signals, and forms ultrasonic beams for one or more convergent points. The signal processing section 105 is fed with the reception signals from the phasing addition circuit 104 and performs various kinds of signal processing such as gain correction, log compression, detection, edge enhancement, and filter processing.

The monochrome scan converter 106 obtains RF signal frame data in the test subject 100 including motor tissue in an ultrasonic cycle by using a reflecting echo signal outputted from the signal processing section 105 of the ultrasonic wave transmitter/receiver section, and the monochrome scan converter 106 displays the RF signal frame data on the image display device 107 via the change-over adder 114. One RF signal frame data constitutes an image. Therefore, the monochrome scan converter 106 includes a tomographic scanning section for sequentially reading RF signal frame data in a cycle of television system and various control circuits for controlling a system. For example, the monochrome scan converter 106 includes an A/D converter for converting the reflecting echo signal from the signal processing section 105 into a digital signal, a plurality of frame memories for storing tomographic image data, which has been digitized by the A/D converter, in time sequence, and a controller for controlling these operations.

The image display device 107 displays the time-sequence tomographic image data having been obtained by the monochrome scan converter 106. The image display device 107 is constituted of a D/A converter for converting image data, which is outputted from the monochrome scan converter 106 via the change-over adder 114, into an analog signal, and a color television monitor which is fed with an analog video signal from the D/A converter and displays the signal as an image.

In this embodiment, the RF signal frame data selection section 108 and the displacement measurement section 109 are disposed so as to branch off from the output side of the phasing addition circuit 104, and the pressure measurement section 110 is provided in parallel with the RF signal frame data selection section 108 and the displacement measurement section 109. The distortion/elastic modulus calculation section 111, the elastic data processing section 112, and the color scan converter 113 are provided in the subsequent stages of the displacement measurement section 109 and the pressure measurement section 110. The change-over adder 114 is provided on the output side of the color scan converter 113 and the monochrome scan converter 106.

Figure 2:
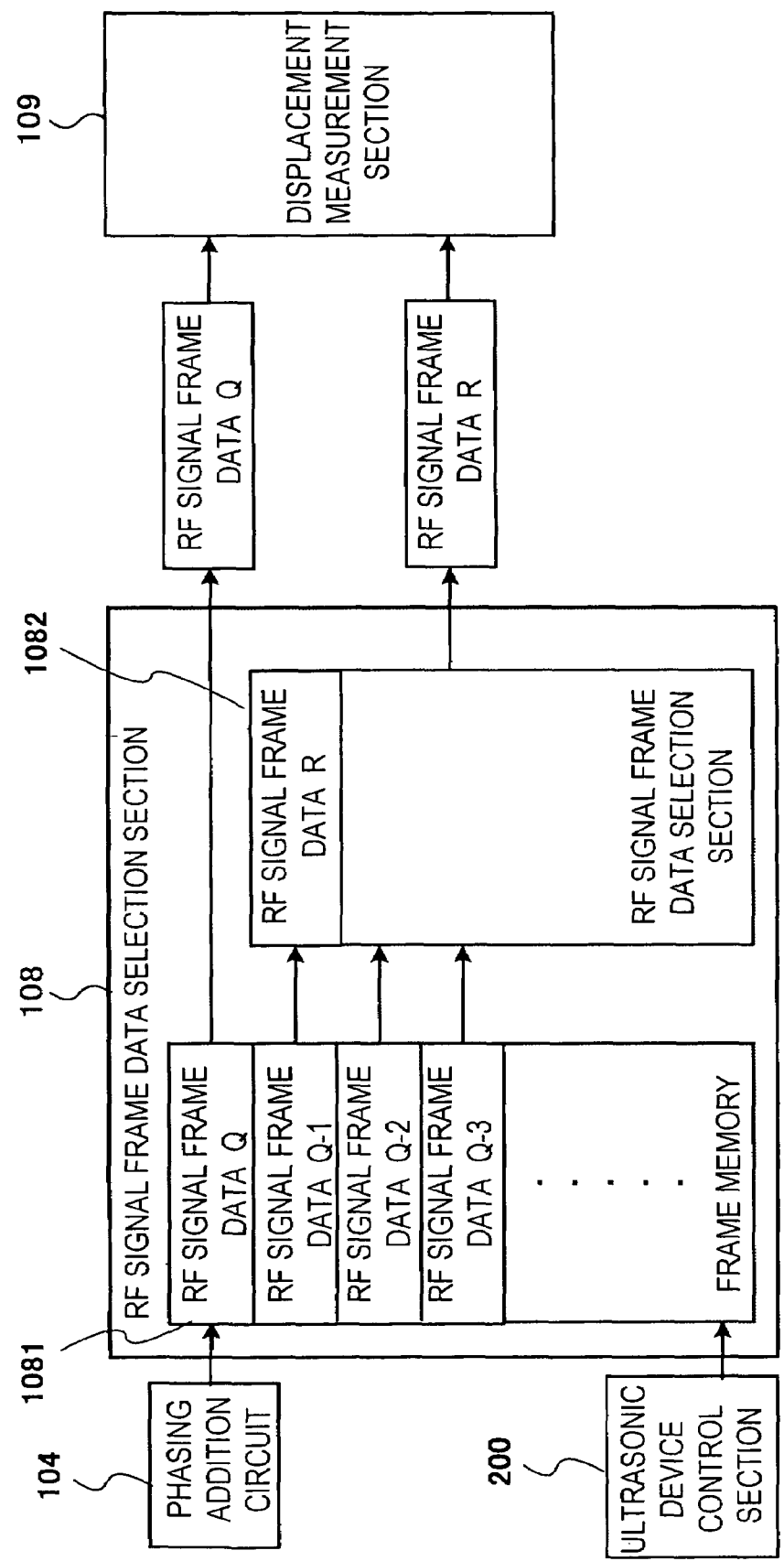
FIG. 2 is a diagram showing an example of an RF signal frame data selection section shown in FIG. 1.

Referring to FIG. 2, the operations of the RF signal frame data selection section 108 will be discussed below according to the present embodiment. FIG. 2 is a diagram showing an example of the RF signal frame data selection section of FIG. 1. The RF signal frame data selection section 108 arbitrarily selects the number of past frames (the number of frame intervals from the current frame data) as one RF signal frame data serving as the reference of displacement measurement. In other words, the RF signal frame data selection section 108 sequentially obtains RF signal frame data, which is successively outputted from the phasing addition circuit 104 in time sequence at the frame rate of the ultrasonographic device, in a frame memory 1081. The RF signal frame data selection section 108 sets the latest data, which is currently obtained in the frame memory 1081, as RF signal frame data Q. The RF signal frame data selection section 108 selects one of the past RF signal frame data Q-1, Q-2, Q-3, . . . , and Q-M in response to a control command from a control section 200 of the ultrasonographic device, and temporarily stores the data as RF signal frame data R in an RF signal frame data selection circuit 1082. The RF signal frame data selection section 108 outputs in parallel the latest RF signal frame data Q stored in the frame memory 1081 and the RF signal frame data R stored in the RF signal frame data selection circuit 1082 to the displacement measurement section 109.

In other words, first, the RF signal frame data selection section 108 can arbitrarily select not only the RF signal frame data Q-1, which temporally adjoins to the current RF signal frame data Q, but also the RF signal frame data Q-M, which is obtained by thinning out M frames (M=1, 2, 3, . . . ), as the past RF signal frame data R constituting a group of RF signal frame data to be sent to the displacement measurement section 109. Besides, M frame intervals (M=1, 2, 3, . . . ) can be arbitrarily set and changed by the user interface of the ultrasonographic device when a change in pressure applied to an examinee through the ultrasonic wave transmitter/receiver section cannot be sufficiently large.

Figure 3:
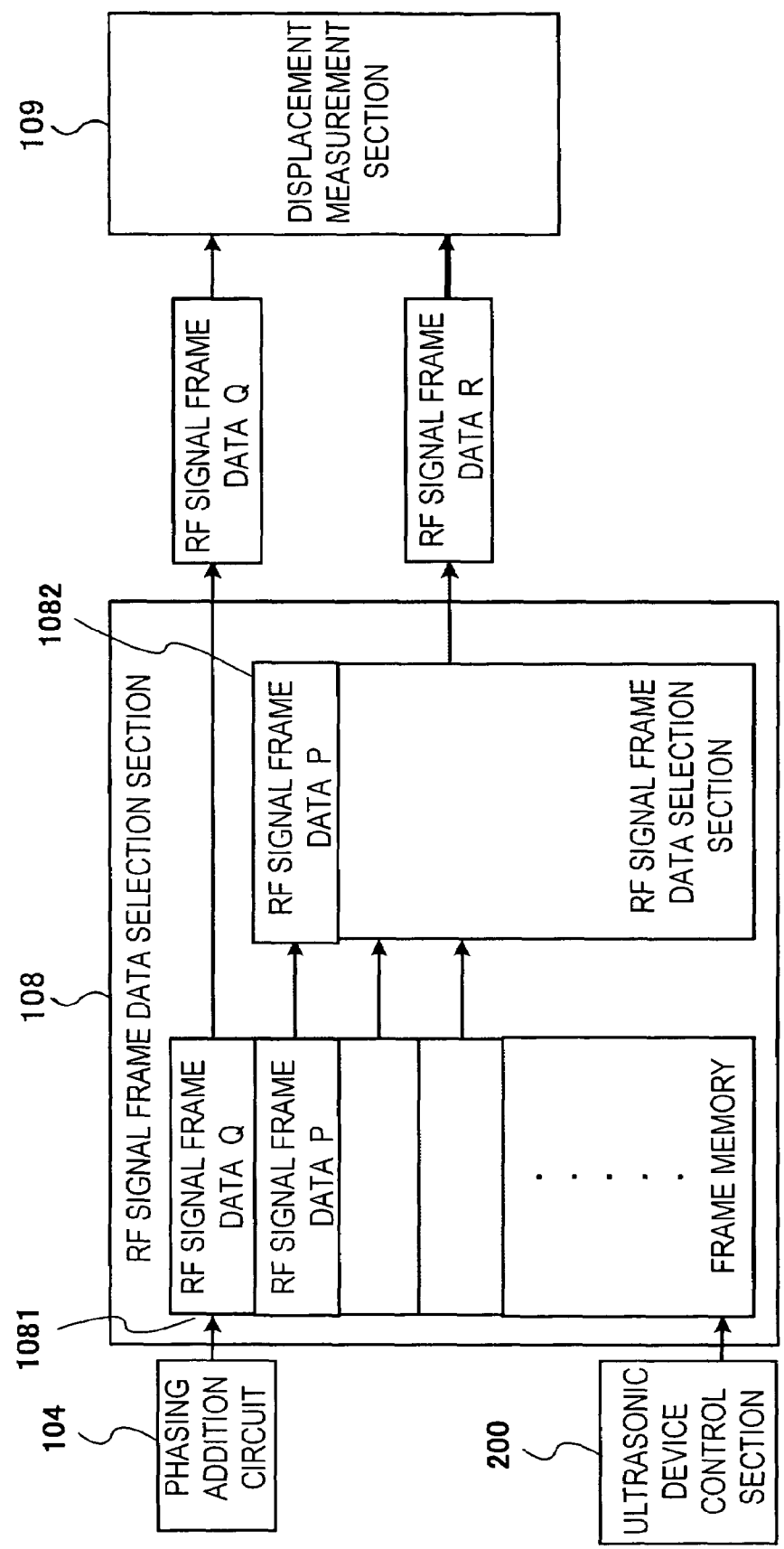
FIG. 3 is a diagram showing another example of the RF signal frame data selection section shown in FIG. 1.

FIG. 3 is a diagram showing another example of the RF signal frame data selection section of FIG. 1. The RF signal frame data selection section 108 of FIG. 3 obtains RF signal frame data P, which has been obtained in a certain time phase P of the past, in the frame memory 1081 in response to a control command from the control section 200 of the ultrasonographic device. The RF signal frame data selection circuit 1082 always refers to the RF signal frame data P, which is obtained in the frame memory 1081, as past RF signal frame data in a given time phase without updating. Therefore, the displacement measurement section 109 obtains a group of RF signal frame data constituted of the currently obtained RF signal frame data Q and the RF signal frame data P. Regarding whether to use the function of FIG. 3 or the setting of the timing for obtaining the RF signal frame data P when the function is used, it is possible to freely make a switching, setting, and change by the user interface of the ultrasonographic device when a change in pressure applied to the examinee through the ultrasonic transmit/receive section cannot be increased sufficiently.

When an interval between past and current RF signal frame data constituting a group of RF signal frame data is limited to adjacent frames, an amount of pressurization or decompression applied in a time interval between the RF signal frame data may not sufficiently reach an amount of pressurization or decompression (generally about 1%) suitable for visualizing elastic image data. The RF signal frame data constitutes a group of two or more RF signal frame data having been obtained during a series of pressurizing or decompressing operations. In contrast, with the RF signal frame data selection section shown in FIGS. 2 and 3, it is possible to sufficiently increase a frame interval between past and current RF signal frame data, thereby properly visualizing an elastic image of elastic frame data. The RF signal frame data selection section is particularly useful in a state in which a pressuring or decompressing speed cannot be sufficiently increased in a series of pressurizing or decompressing operations in ultrasonography due to a physical restriction of the build of the examinee. The frame interval can be arbitrarily set and changed after the user confirms a change of an elastic image.

The displacement measurement section 109 performs a one-dimensional or two-dimensional correlation operation based on the group of RF signal frame data having been selected by the RF signal frame data selection section 108, and measures a displacement or a mobile vector (the direction and amount of a displacement) of each point on a tomographic image. A method of detecting the mobile vector includes, e.g., a block matching method and a gradient method which are described in JP-A-5-317313. In the block matching method, an image is divided into, e.g., blocks of N×N pixels, the previous frame is searched for a block the most analogous to a noticed block in the current frame, and predictive coding is performed with reference to the block.

Also, a displacement or a mobile vector of each point on a tomographic image can be determined based on an amount of movement of the probe from a surface of the test subject.

The amount of movement of the probe can be determined using a transmitter and a receiver, each of which has a unique coordinate space of a three-axis orthogonal system as disclosed in JP-A-10-151131. When the receiver is disposed in the probe and the transmitter is disposed near the test subject so as not to move, it is possible to locate the receiver in the coordinate space set by the transmitter. With this configuration, it is possible to obtain the amount of movement of the probe which moves with a pressure applied to the test subject. For example, the transmitter can be composed of a magnetic field generating coil for generating a magnetic field of the three-axis orthogonal system, and the receiver can be composed of a detection coil capable of detecting a magnetic field of the three-axis orthogonal system. The transmitter and the receiver are disposed such that the coil surfaces of the magnetic field generating coil and the magnetic field detection coil of the three-axis orthogonal system are orthogonal to each other. Alternating current is applied to each coil of the transmitter to generate an alternating magnetic field. The generated alternating magnetic field is detected by the detection coil of the receiver. Each directional component of the detected magnetic field and the intensity of the magnetic field are calculated by an arithmetic unit (not shown), so that the positional relationship between the transmitter and the receiver can be recognized. The amount of movement of the probe is calculated based on the calculated positional relationship and is reflected on RF frame data to obtain elastic frame data. Alternatively, elastic frame data is obtained from the calculated amount of movement.

Figure 4:
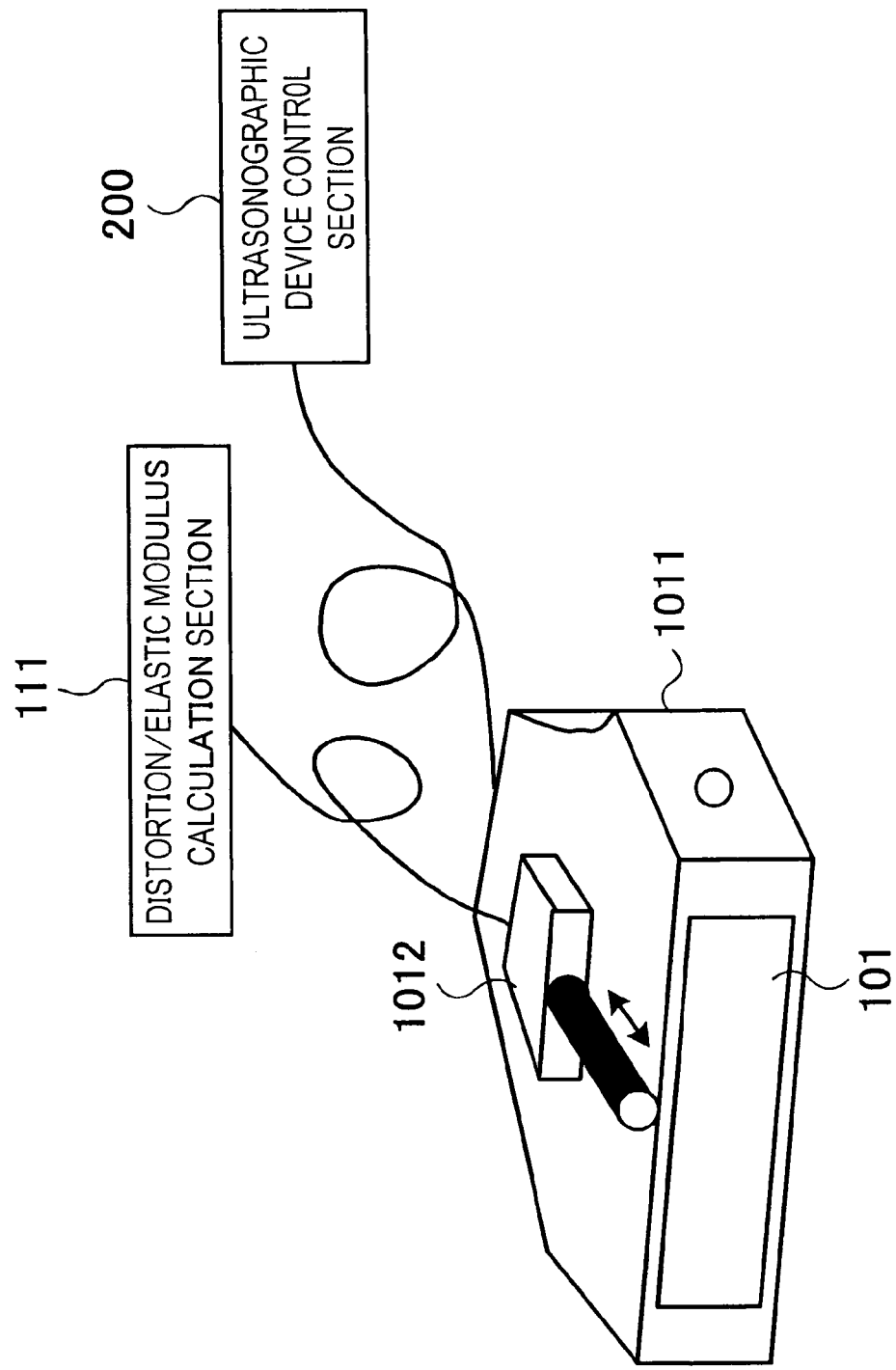
FIG. 4 is a diagram showing an example of a method of measuring a pressure between the head of an ultrasound probe and a test subject by means of a pressure measurement section (pressure sensor) attached to the probe.

The pressure measurement section 110 measures or estimates the in vivo pressure of an examined part of the test subject 100. In the ultrasonographic device, the following method is used: while ultrasonic waves are transmitted and received under the control of the control section 200 by using the ultrasound probe 101 disposed on the probe head 1011, a pressure is increased or reduced by using a pressurizer 115 disposed on a probe head 1011, so that a stress distribution is provided in the body cavity of the examined part of the test subject 100. In this method, in order to measure a pressure applied between the probe head 1011 and the test subject 100, a pressure sensor 1012 for detecting a pressure applied to a rod-like member is attached to, e.g., the side of the probe head 1011 as shown in FIG. 4, a pressure between the probe head 1011 and the test subject 100 is measured in a given time phase, and a measured pressure value is transmitted to the distortion/elastic modulus calculation section 111. In FIG. 4, the pressurizer 115 may be provided which is attached to the probe head 1011 and automatically pressurizes or decompresses a living body.

The distortion/elastic modulus calculation section 111 calculates a distortion and an elastic modulus of each point on a tomographic image based on an amount of movement (displacement $\Delta L$) and a change in pressure ($\Delta P$) which are outputted from the displacement measurement section 109 and the pressure measurement section 110, respectively, to generate numeric data of a distortion and an elastic modulus (elastic frame data), and outputs the data to the elastic data processing section 112. When a distortion is calculated by the distortion/elastic modulus calculation section 111, the distortion may be calculated by, e.g., a space differentiation ($\Delta L/\Delta X$) performed on the displacement $\Delta L$ without using pressure data. $\Delta X$ represents a displacement of a coordinate. A Young's modulus Ym, which is one of elastic moduli, may be calculated by the following equation in which a change in pressure is divided by a change in the amount of movement:

$$Ym = (\Delta P)/(\Delta L/L)$$

where L represents the original length.

Figure 5:
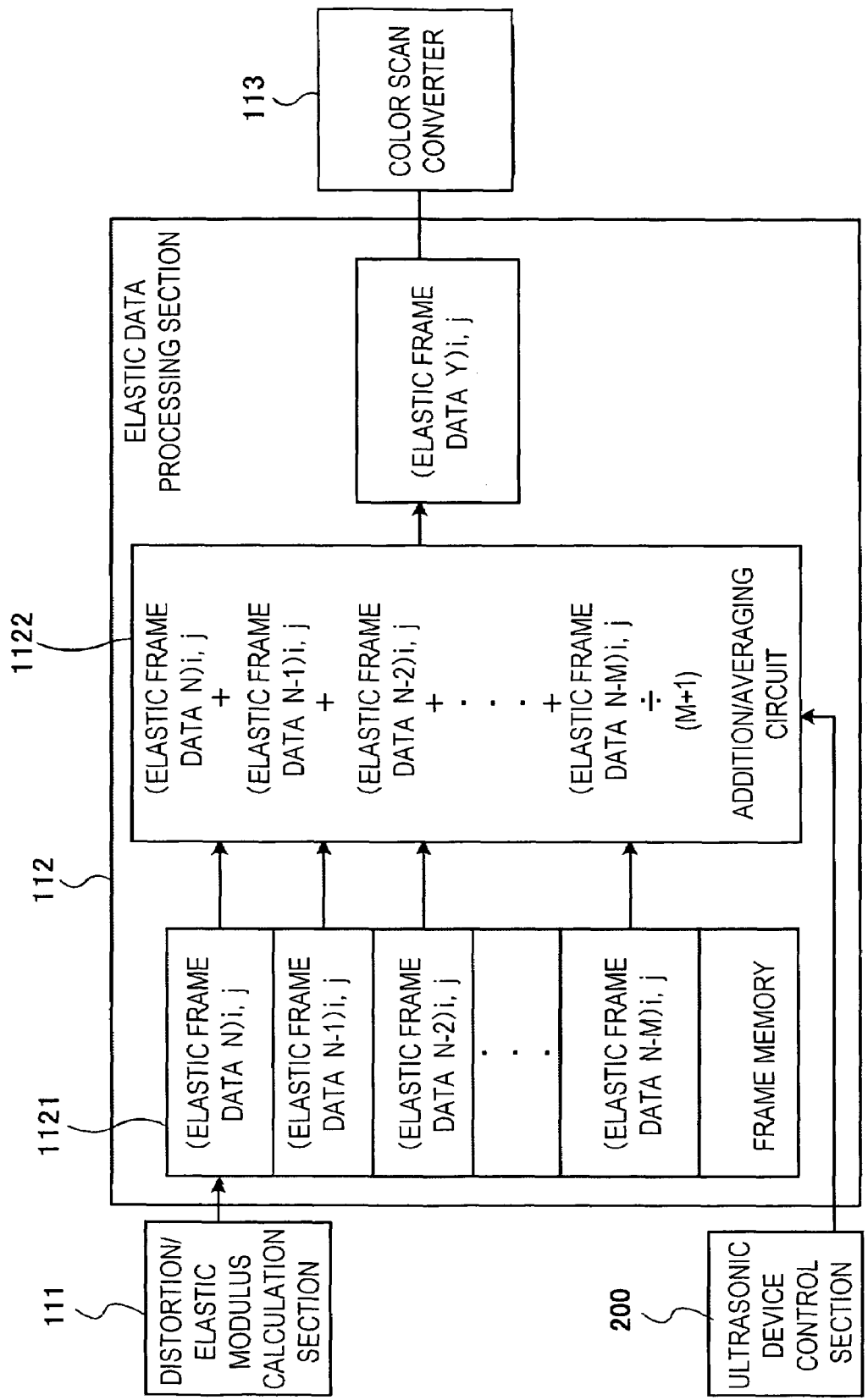
FIG. 5 is a diagram showing an example of the operations of an elastic data processing section shown in FIG. 1.

FIG. 5 is a diagram showing an example of the operations of the elastic data processing section shown in FIG. 1. The elastic data processing section 112 sequentially obtains elastic frame data X, which is successively inputted from the distortion/elastic modulus calculation section 111 in time sequence, in a frame memory 1121. The elastic data processing section 112 sets, as elastic frame data N, elastic frame data currently obtained in the frame memory 1121. Therefore, elastic frame data N, N-1, N-2, ..., N-M are stored in this order in the frame memory 1121 in time sequence. In response to a control command from the control section 200 of the ultrasonographic device, an addition/averaging circuit 1122 selects elastic frame data of M frames in turn, starting from the most analogous data at the present time, out of the elastic frame data having been obtained in the frame memory 1121. The addition/averaging circuit 1122 performs addition and averaging on the same coordinate data point based on the current elastic frame data N, which has been selected from the frame memory 1121, and the past elastic frame data N-1, N-2, ... N-M of M frames. The elastic frame data obtained by the addition and averaging is transmitted as current elastic frame data Y to the color scan converter 113. Regarding the number M of past elastic frame data selected by the addition and averaging on elastic frame data and a decision on whether to use the function of addition and averaging on elastic frame data, it is possible to freely make a setting and change in the user interface of the ultrasonographic device.

The above operations are expressed by the following equation:

$$(\text{elastic frame data } Y)\, i,j = \{(\text{elastic frame data } N)\, i,j + (\text{elastic frame data } N\text{-}1)\, i,j + (\text{elastic frame data } N\text{-}2)\, i,j + \ldots + (\text{elastic frame data } N\text{-}M)\, i,j\} \div (M+1)$$

where indexes i and j represent the coordinates of each frame data.

The addition/averaging circuit 1122 in the elastic data processing section of the present embodiment performs addition and averaging on elastic frame data in the time-base direction. Thus, it is possible to smooth a temporally irregular area of a stress distribution in an object into a continuous area, thereby reducing noise. The irregular area occurs when the object is unevenly pressurized or decompressed in a diagonal direction.

Figure 6:
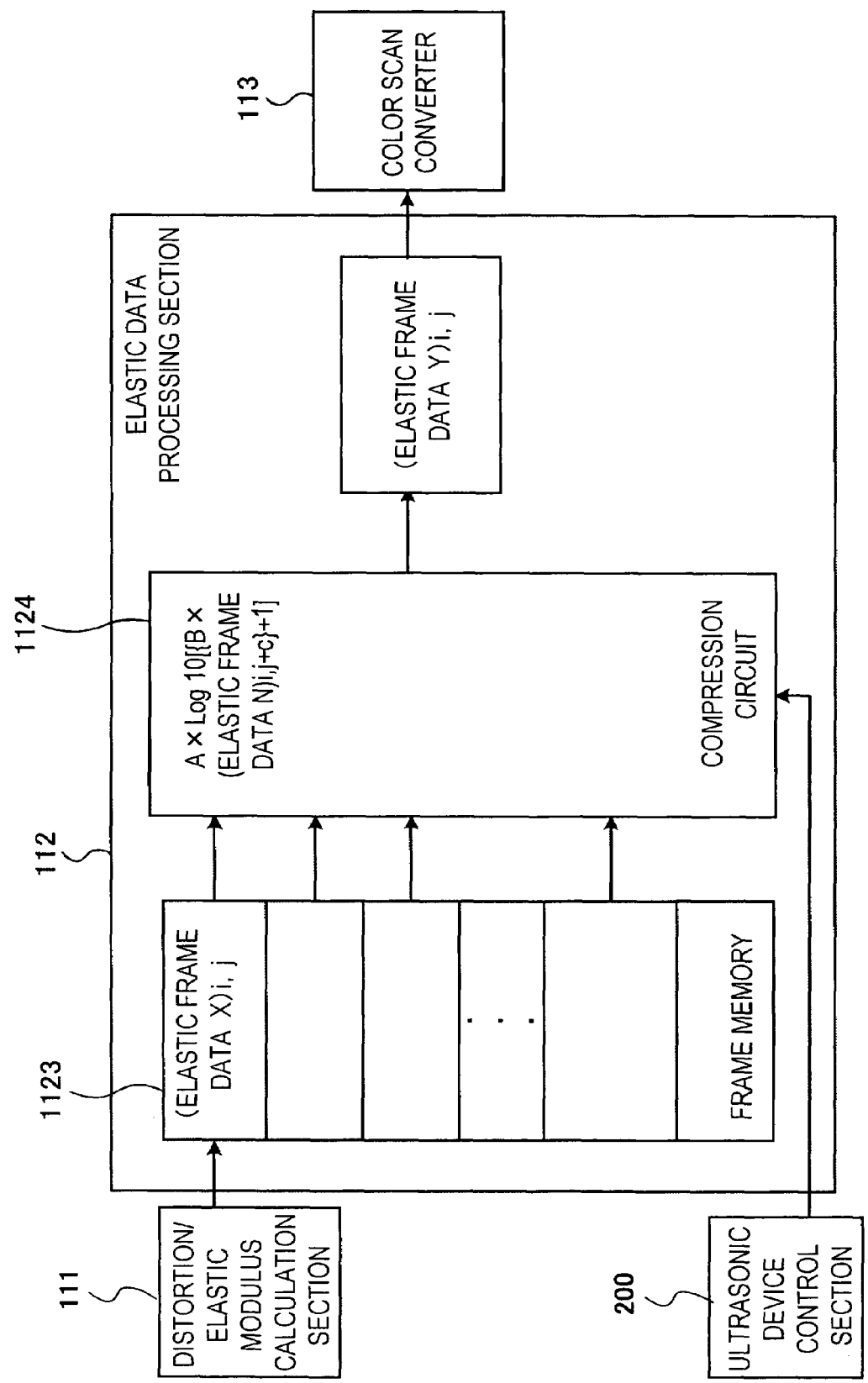
FIG. 6 is a diagram showing another example of the operations of the elastic data processing section shown in FIG. 1.

FIG. 6 is a diagram showing another example of the operations of the elastic data processing section shown in FIG. 1. The elastic data processing section 112 of this example performs logarithmic transformation on inputted elastic frame data. The elastic data processing section 112 obtains elastic frame data X, which is successively outputted from the distortion/elastic modulus calculation section 111 in time sequence, in a frame memory 1123, causes a compression circuit 1124 to perform logarithmic transformation on the data according to a correspondence between elastic image data and elastic frame data reflecting an instruction of a control command from the control section 200 of the ultrasonographic device, and transmits the transformed elastic frame data as elastic frame data Y to the color scan converter 113. When inputted elastic frame data is expressed by [(elastic frame data X) i,j] and outputted elastic frame data is expressed by [(elastic frame data Y) i,j], a logarithm operation performed by the elastic data processing section 112 of FIG. 6 is expressed by the following equation:

$$(\text{elastic frame data } Y)\, i,j = A \times \text{Log}\, 10\, [B \times \{(\text{elastic frame data } X)\, i,j + C\} + 1]$$

where indexes i and j represent the coordinates of each frame data, and A, B, and C represent certain constants. Particularly regarding the combination of the constants A, B, and C in the above equation and a decision whether to use the compressing function, it is possible to freely make a setting and change in the user interface of the ultrasonographic device.

Figure 7:
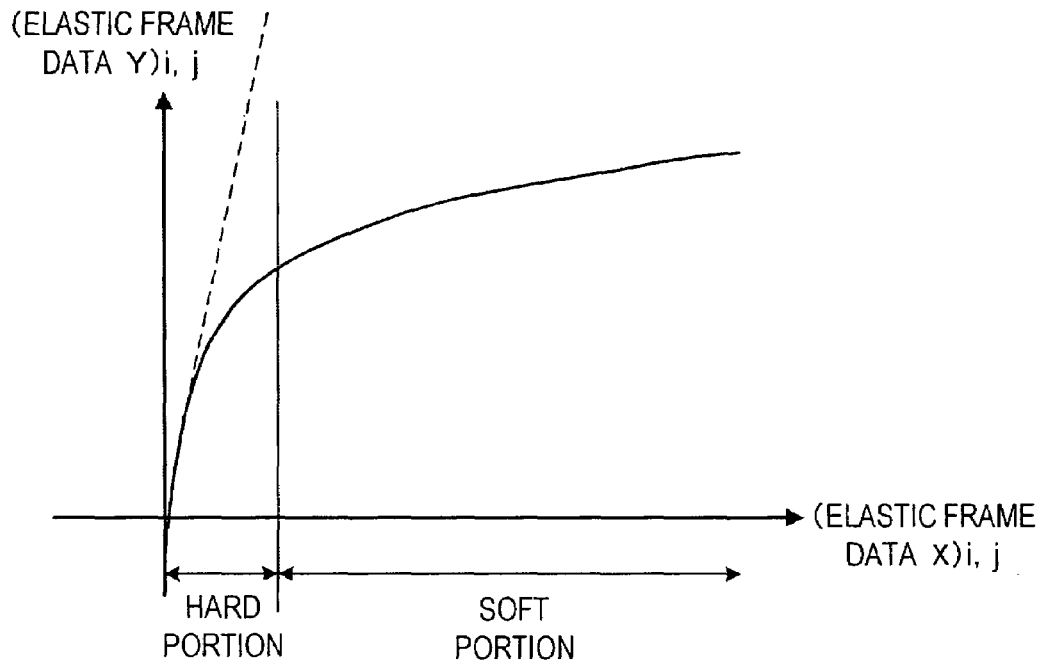
FIG. 7 is a diagram showing a relationship before and after logarithmic transformation on elastic frame data in the elastic data processing section.

Particularly in image diagnosis using elastic images, it is highly significant to clearly detect a hard portion suspected of being a cancer tissue. Thus, it is important to clearly visualize a hard area. There is a report describing a property of a living tissue (T. A. Krouskop et al, Ultrasonic Imaging, 1998). According to this report, an adipose tissue and a cancer tissue are different in hardness by several tens times in, e.g., a mammy gland area. However, regarding the elastic imaging of elastic frame data in hue information converting means for color display or monochrome luminance information converting means for monochrome display in the existing ultrasonographic device, the values of elastic frame data and the values of elastic image data have a linear relationship as indicated by a broken line of FIG. 7. Thus, in the case where a difference in the hardness of tissue is visualized in the same elastic image, in any area selected as an imaging range in elastic frame data, the process of a spatial change in hardness between two areas of a soft area and a hard area can be expressed only by a linear relationship, so that it is difficult to clarify the hard area and recognize the edge of a hardened portion. In other words, only two areas of an extremely soft area and an extremely hard area are clearly visualized like a binarized image, and thus it has been difficult to properly express a large change in hardness from the soft area to the hard area as hue information or monochrome luminance information. Therefore, in some cases, it is difficult to determine the size of a hardened cancer tissue in elastic image diagnosis. In contrast, according to the above-described embodiment in which the compression circuit 1124 is used in the elastic data processing section 112, as indicated by a solid line of FIG. 7, an area having small values (hard area) becomes elastic frame data of values sharply changing in a coordinate space and an area having large values (soft area) becomes elastic frame data of values gradually changing in the coordinate space in inputted elastic frame data. When elastic image data is generated based on elastic frame data outputted from the elastic data processing section 112, it is possible to clearly display a hard area, thereby recognizing the edge of a hardened portion.

Figure 8:
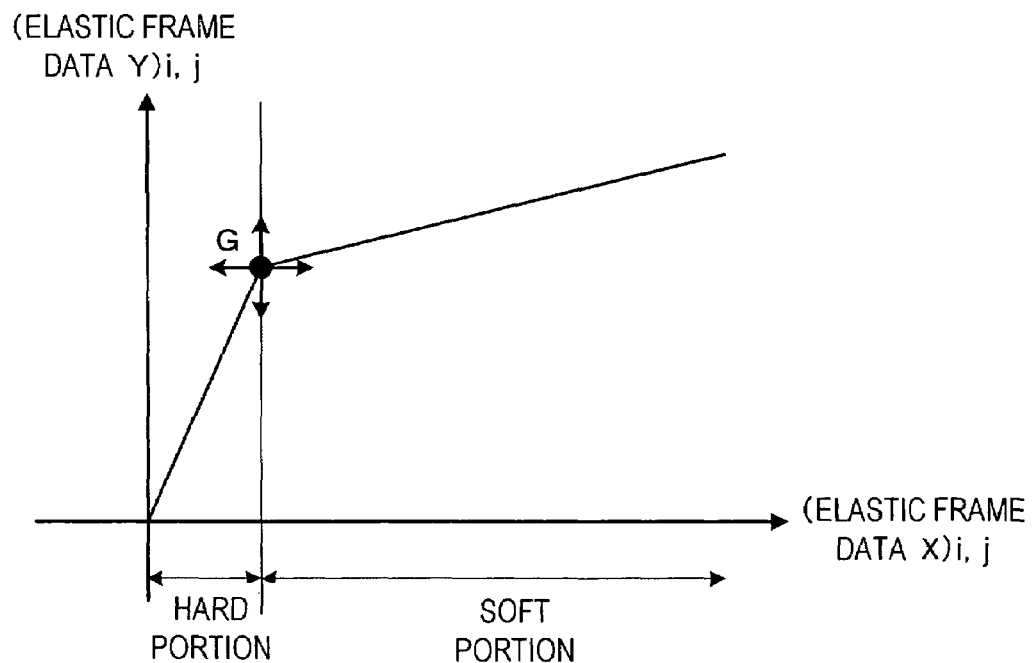
FIG. 8 is a diagram showing an example in which two or more functions are combined to transform elastic frame data in the elastic data processing section.

Logarithmic transformation was described as an example of data conversion performed by the compression circuit 1124 of the elastic data processing section 112 shown in FIG. 6. Compression may be performed using another transfer function having a property enabling the above-described object. For example, $Y = A \times (1 - \text{Exp}(-B \times X))$ or the like may be used where A and B represent constants. Further, several kinds of transfer functions may be prepared and freely set and changed by the user interface of the ultrasonographic device. Moreover, one transfer function may be composed of, e.g., two or more curves as shown in FIG. 8. In the function of FIG. 8, an intersection point G may be freely set and changed vertically and horizontally. Hence, it is possible to freely set the sensitivity of a hard portion and a soft portion.

Figure 9:
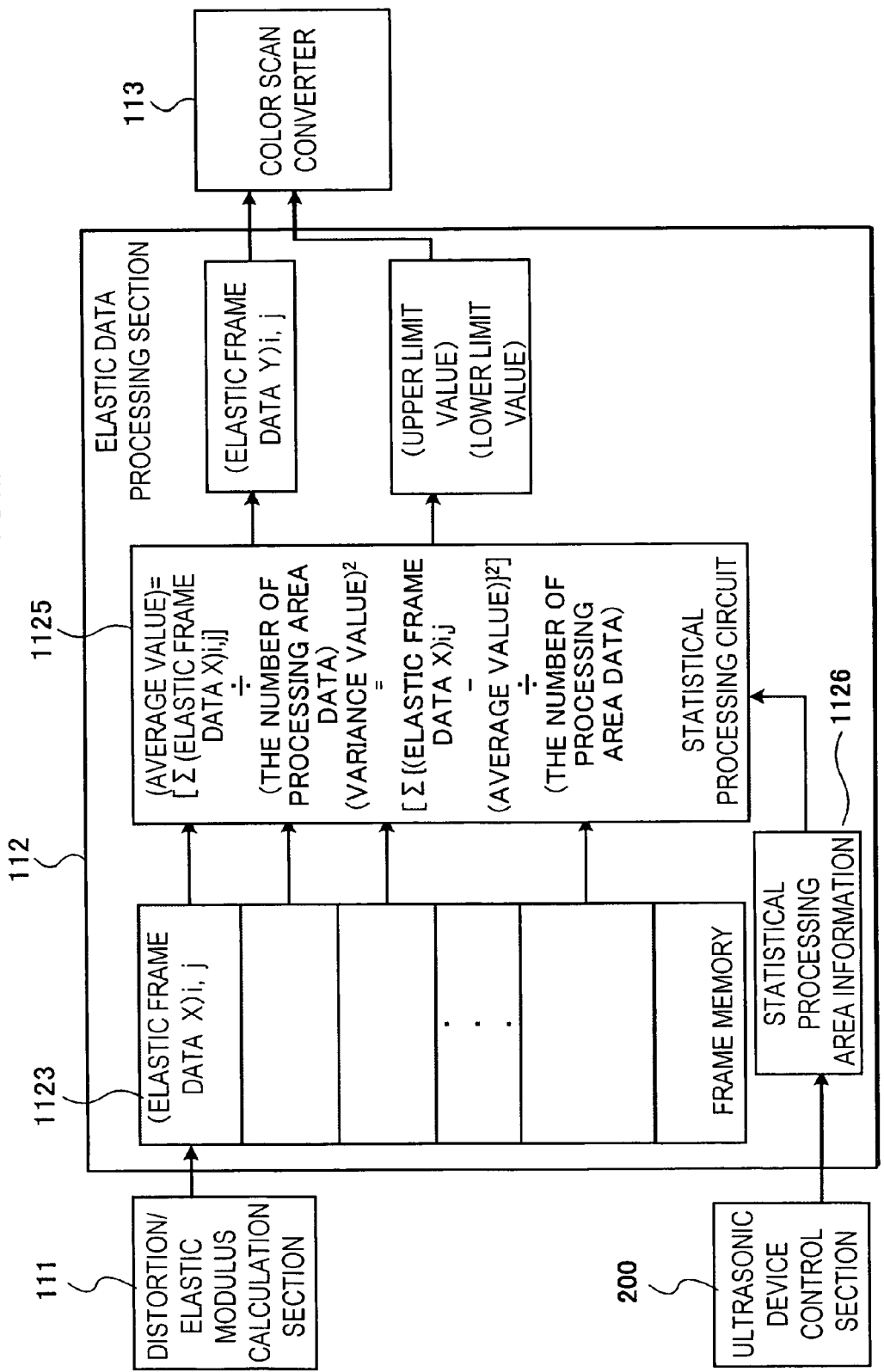
FIG. 9 is a diagram showing another example of the operations of the elastic data processing section shown in FIG. 1.

FIG. 9 is a diagram showing still another example of the operations of the elastic data processing section 112 shown in FIG. 1. The elastic data processing section 112 of FIG. 9 performs statistical processing on inputted elastic frame data. Specifically, the elastic data processing section 112 of FIG. 9 obtains elastic frame data X, which is successively outputted from the distortion/elastic modulus calculation section 111 in time sequence, in the frame memory 1123 of the elastic data processing section 112. In a coordinate area of elastic frame data reflecting an instruction of a control command (statistic processing area information 1126) from the control section 200 of the ultrasonographic device, a statistical processing circuit 1125 of the elastic data processing section 112 performs statistical processing on the elastic frame data. The statistical processing circuit 1125 determines, based on a statistical characteristic amount obtained as a result, the upper limit value and the lower limit value of the elastic frame data selected as the range of image data when elastic image data is generated, and transmits elastic frame data Y and the upper and lower limit values to the color scan converter 113. The elastic frame data Y may be given elastic frame data X or an average value of a processing area.

As a statistical characteristic amount in the statistical processing circuit 1125 of FIG. 9, for example, an average value and a variance value may be obtained. The average value and the variance value are expressed by the following equation:

$$\text{(average value)} = [\Sigma(\text{elastic frame data } X)\, i,j] \div (\text{the number of processing area data})$$
$$(\text{variance value})^2 = [\Sigma\{(\text{elastic frame data } X)\, i,j - (\text{average value})\}^2] \div (\text{the number of processing area data})$$

where [(elastic frame data X) i,j] represents inputted elastic frame data. In this equation, $\Sigma$ represents a sum of data elements in the coordinate area of elastic frame data reflecting the statistical processing area information 1126, which is a control command from the control section 200 of the ultrasonographic device.

As the upper limit value and the lower limit value of elastic frame data selected as a range of image data during the generation of elastic image data, the following may be obtained:

$$(\text{upper limit value}) = (\text{average value}) + (\text{constant } D) \times (\text{variance value})$$

$$\{\text{or (upper limit value)} = (\text{constant } D') \times (\text{average value})\}$$

$$(\text{lower limit value}) = (\text{average value}) - (\text{constant } E) \times (\text{variance value})$$

$$\{\text{or (lower limit value)} = (\text{constant } E') \times (\text{average value})\}$$

The obtained upper limit value and lower limit value may be transmitted to the color scan converter 113. The constant D or D' and the constant E or E' may be freely set and changed in the user interface of the ultrasonographic device. Further, one of the upper limit value and the lower limit value may be set by the above equations and the other may be set at a fixed value not reflecting the statistical characteristic of elastic frame data. For example, the lower limit value may be fixed at a distortion amount of 0% and the upper limit value may be set to average value+2×variance value.

Figure 10:
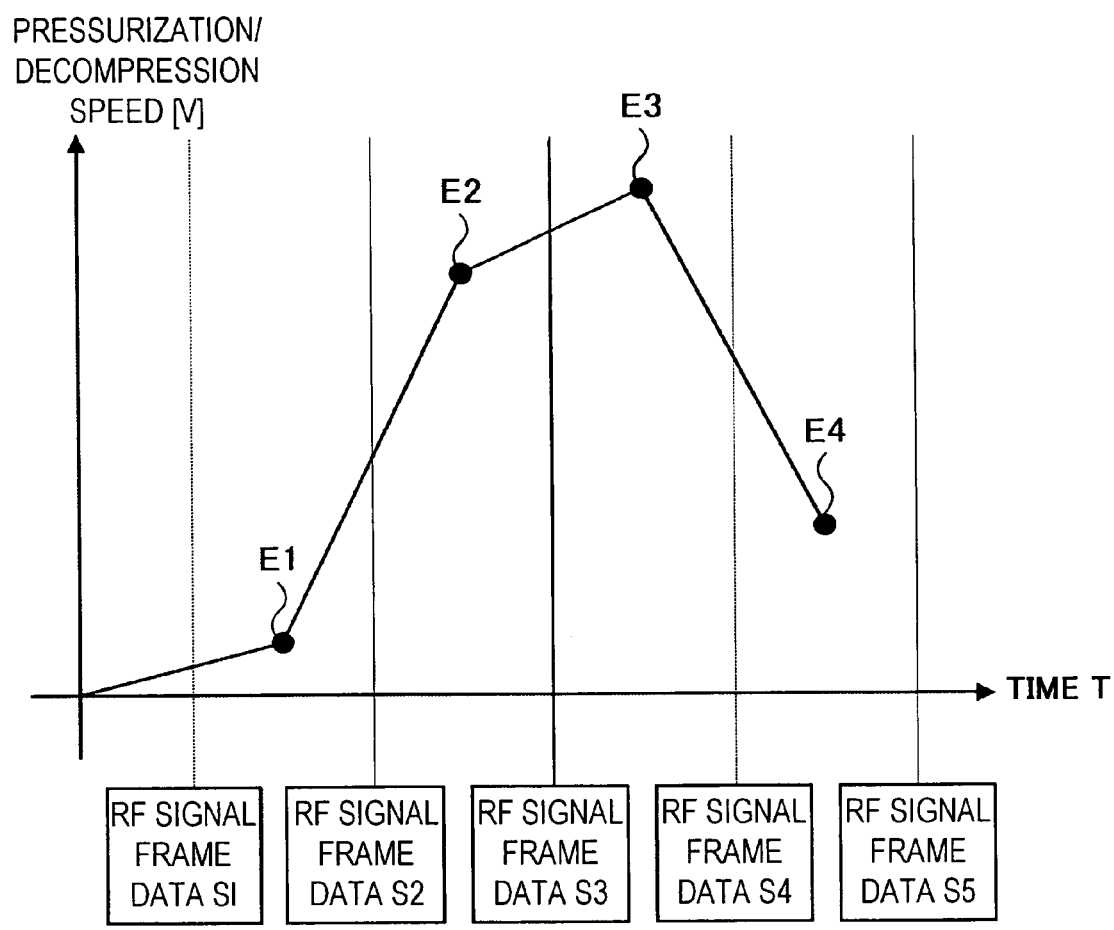
FIG. 10 is a diagram showing an example of the relationship between a temporal change in pressurization/decompression speed and the timing for obtaining an RF signal.

FIG. 10 is a diagram showing an example of the relationship between a temporal change in pressurization/decompression speed and the timing for obtaining an RF signal. As is evident from FIG. 10, when a pressurization or decompression speed V varies during a series of pressurizing or decompressing operations, the same coordinate region of elastic frame data E1 to E4 has a statistical distribution (histogram) schematically shown based on the same scale in FIGS. 11A and 11B. Elastic frame data calculated by a pair of RF signal frame data S1 and RF signal frame data S2 is represented as E1, elastic frame data calculated by a pair of RF signal frame data S2 and RF signal frame data S3 is represented as E2, elastic frame data calculated by a pair of RF signal frame data S3 and RF signal frame data S4 is represented as E3, and elastic frame data calculated by a pair of RF signal frame data S4 and RF signal frame data S5 is represented as E4. The vertical axis represents the number of data elements and the horizontal axis represents a distortion amount.

Figure 11:
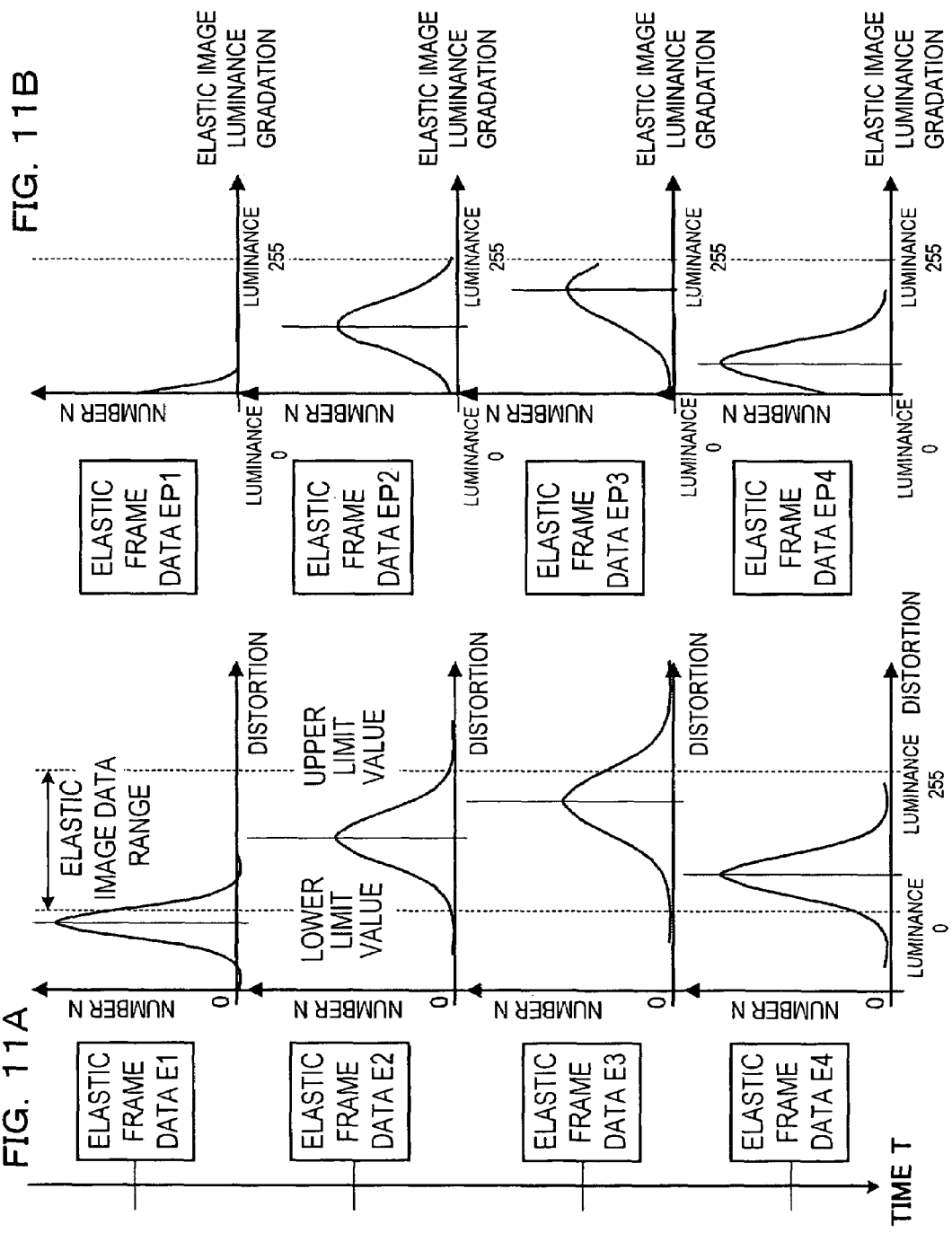
FIGS. 11A and 11B are diagrams showing a temporal change of an elastic image luminance distribution when the upper limit value and the lower limit value of elastic frame data are set in a fixed manner.

As shown in FIG. 11A, in a series of elastic frame data having been obtained in time series, the elastic frame data E1 to E4 of the same area changes over time. In other words, when a pressurization or decompression speed varies during a series of pressurizing or decompressing operations, elastic frame data of the same area varies according to a change in pressurization or decompression speed, in the series of elastic frame data having been obtained in time sequence. In the elastic imaging of elastic frame data in the hue information converting means and the monochrome luminance information converting means of the conventional ultrasonographic device, the values of elastic frame data and the values of elastic image data are fixed in a one-to-one correspondence. For example, elastic image data EP1 to EP4 are generated while the upper limit value and the lower limit value obtained by optimization using the elastic frame data E2 of FIGS. 11A and 11B are used as the upper limit value and the lower limit value of the elastic frame data E1 to E4 in a given time phase. In this case, in the time phase of the elastic frame data E3, the elastic image data EP3 is obtained by which an area calculated with a relatively large distortion is not imaged. Conversely, in the time phase of the elastic frame data E1, the elastic image data EP1 is obtained by which an area calculated with a relatively small distortion is not imaged. Unlike a time phase when the elastic frame data E2 is obtained, elastic image data like the elastic image data EP2 of optimized gradation cannot be always generated in a given time phase.

Figure 12:
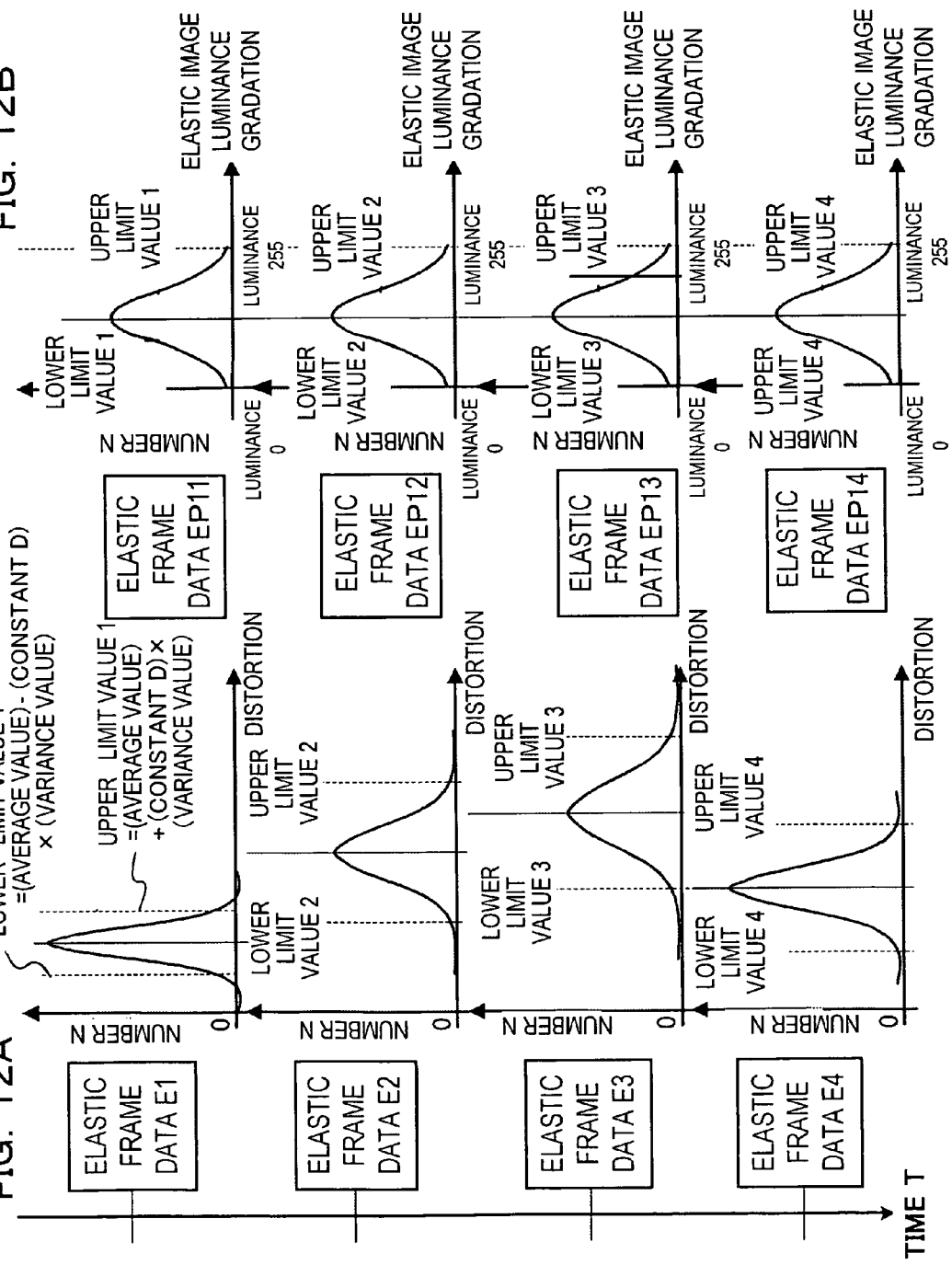
FIGS. 12A and 12B are diagrams showing a temporal change of the elastic image luminance distribution when the upper limit value and the lower limit value of the elastic frame data are properly set under statistically shared conditions in the elastic data processing section of FIG. 9.

In this way, in the elastic imaging of elastic frame data in the color scan converter of the conventional ultrasonographic device, when a pressurization or decompression speed varies, an image (FIG. 11B) is obtained which varies in monochrome luminance or hue in the same area of a series of elastic image data having been obtained in time sequence, so that image diagnosis becomes difficult. In other words, in all time phases, the fixed correspondence does not always optimize the contrast of an elastic image. In contrast, when the pressurization or decompression speed V varies during a series of pressurizing or decompressing operations as shown in FIG. 10, the statistical processing circuit of the elastic data processing section of FIG. 9 performs statistical processing on elastic frame data in a given time phase, and sets the upper limit value and the lower limit value of an imaging range according to the statistical characteristic amount. For example, (average value)±(constant D)×(variance value) shown in FIG. 12A is calculated as an imaging range for the elastic frame data of a given time phase. In this case, the constant D is a shared value in the given time phase. Thus, the optimum imaging range is set for each of the elastic frame data.

The statistically shared upper and lower limit values having been obtained thus for elastic frame data in a given time phase are transmitted to the color scan converter, and elastic image data is generated within the range from the upper limit value to the lower limit value, so that elastic image data EP11 to EP14 can be generated with the efficient gradation of elastic frame data elements in a given time phase as shown in FIG. 12B. With the statistical processing circuit in the elastic data processing section of the present embodiment, even when a pressurization or decompression speed varies, it is possible to reduce a change in the monochrome luminance or hue of the same area in a series of elastic image data having been obtained in time sequence, and provide an image with predetermined display gradation which is temporally stable, thereby facilitating image diagnosis. In other words, a ratio of the number of pixels exceeding the upper limit value of display gradation in elastic image data and a ratio of the number of pixels falling below the lower limit value can be standardized to a fixed distribution curve in a given time phase, and an image can be obtained with a smaller change in monochrome luminance or hue.

In FIGS. 12A and 12B, elastic image data is generated such that an average value of the distortions of elastic frame data matches with the center of a predetermined display gradation range.

The foregoing embodiment described, as one of the operations of the RF signal frame data selection section, the case where a pair of RF signal frame data is selected and the number of frame intervals between the pair of RF signal frame data is made variable. Further, the foregoing embodiment described, as an example of an operation in the elastic data processing section, the case where statistical processing is performed on elastic frame data in the statistical processing circuit provided in the elastic data processing section. The following will describe the case where the RF signal frame data selection section and the elastic data processing section operate in cooperation with each other.

Figure 13:
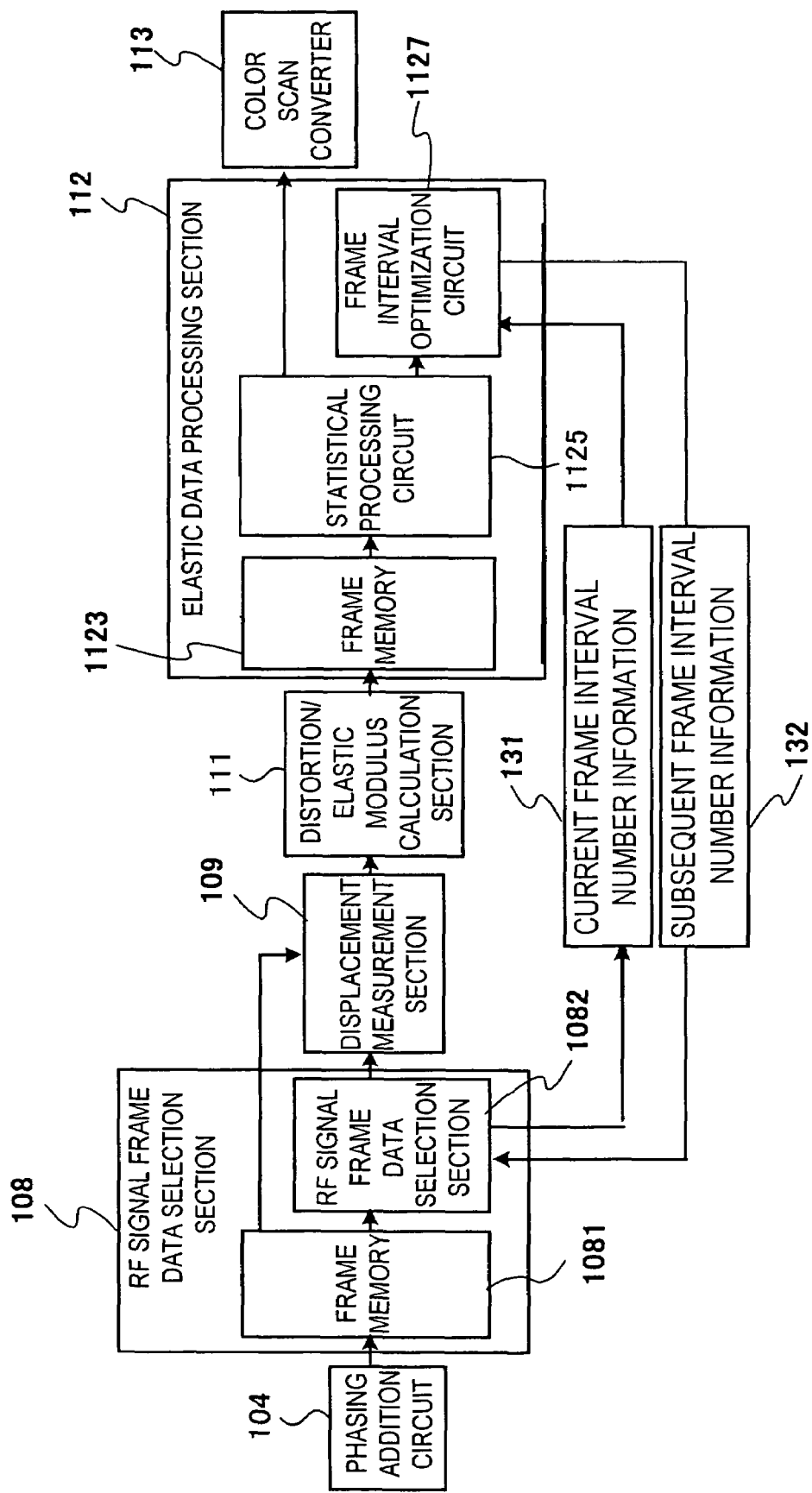
FIG. 13 is a diagram showing an example of the cooperative operations of the RF signal frame data selection section and the elastic data processing section.

FIG. 13 is a diagram showing an example of the cooperative operation of the RF signal frame data selection section and the elastic data processing section. First in the RF signal frame data selection section 108, information (current frame interval number information 131) on the number of frame intervals between a pair of RF signal frame data used for generating current elastic frame data is transmitted to a frame interval optimization circuit 1127 of the elastic data processing section 112. Further, the statistical processing circuit 1125 of the elastic data processing section 112 performs statistical processing on current elastic frame data and transmits information on a statistical characteristic amount as a processing result to the frame interval optimization circuit 1127. Based on the current frame interval number information 131 outputted from the RF signal frame data selection circuit 1082 and the information on the statistical characteristic amount of the current elastic frame data from the statistical processing circuit 1125, the frame interval optimization circuit 1127 calculates the optimum number of frame intervals between a pair of RF signal frame data used for generating the subsequent elastic frame data, and feeds back information on the optimum number of frame intervals as subsequent frame interval number information 132 to the RF signal frame data selection circuit 1082. The RF signal frame data selection circuit 1082 sets the number of frame intervals between the pair of RF signal frame data used for generating the subsequent elastic frame data, based on the optimum number of frame intervals (subsequent frame interval number information 132), the optimum number being outputted from the frame interval optimization circuit 1127.

The following will describe an example of the operations of the frame interval optimization circuit 1127. The number of frame intervals (the current number of frame intervals) of a pair of RF signal frame data for generating current elastic frame data and an average value of distortion amounts as a statistical processing result of the current elastic frame data are inputted to the frame interval optimization circuit 1127.

When a constant H is set to 0.5 to 2.5, the optimum number of frame intervals is determined by the equation below:

(the optimum number of frame intervals)=(constant $H$)×(the current number of frame intervals)÷(average value of distortion amounts)

The closest natural number to the optimum number of frame intervals obtained thus is transmitted to the RF signal frame data selection circuit 1082 as information (subsequent frame interval number information 132) on the number of frame intervals of a pair of RF signal frame data for generating the subsequent elastic frame data. For example, when the constant H is set to "1", the number of frame intervals expected to have a distortion amount of about 1% in the subsequent elastic frame data is transmitted to the RF signal frame selection section.

In image diagnosis using an elastic image, the contrast resolution of a hard area and a soft area considerably depends on a pressurization or decompression amount which is physically applied in a time interval during which a pair of RF signal frame data is obtained. Generally, it is said that an elastic image having the highest contrast resolution is consequently obtained in the range of pressurization or decompression amounts enabling a distortion amount of about 0.5 to 2.5%. As described in the embodiment shown in FIG. 13, when the RF signal frame data selection section 108 and the frame interval optimization circuit 1127 of the elastic data processing section 112 are configured in a cooperative manner, even in a process where a large or small pressure is added or reduced so instantly as to considerably deviate from the optimum range of distortion amounts as an elastic image, such a state is instantly handled by optimizing the number of frame intervals between a pair of RF signal frame data, thereby visualizing a temporally stable elastic image with high contrast resolution.

The color scan converter 113 comprises a hue information conversion section which is fed with elastic frame data outputted from the elastic data processing section 112 and a command outputted from the control section 200 of the ultrasonographic device or the upper and lower limit values for determining a gradation selection range in elastic frame data outputted from the elastic data processing section 112, and which adds hue information of red, green, blue and the like when elastic image data is generated from the elastic frame data. For example, in elastic frame data outputted from the elastic data processing section 112, the hue information conversion section operates so as to convert an area having a large measured distortion into a red code in the elastic image data and conversely converts an area having a small measured distortion into a blue code in the elastic image data. The color scan converter 113 may be constituted of the monochrome scan converter 106. In this case, the area having a large measured distortion is increased in luminance in the elastic image data and conversely the area having the small measured distortion is reduced in luminance in the elastic image data. The elastic image data may be generated using the RF signal frame data selection section 108 of FIGS. 2 and 3, the color scan converter 113, and the elastic data processing section constituted of a combination of two or more elastic data processing sections operating in different manners as shown in FIG. 5, 6, 9, or 13.

Further, the change-over adder 114 is means which is fed with monochrome tomographic image data from the monochrome scan converter 106 and color elastic image data from the color scan converter 113 and adds or switches images. Switching is made such that only monochrome tomographic image data or color elastic image data is outputted or both image data is outputted after addition. For example, as described in JP-A-2000-60853, a monochrome tomographic image and a color elastic image or a monochrome elastic image obtained by the monochrome scan converter may be simultaneously displayed on dual display. Image data outputted from the change-over adder 114 is outputted to the image display device 107.

As another display example of an image, a monochrome tomographic image and a monochrome elastic image may be transmitted to the image display device 107 without addition to display a monochrome tomographic image and a color elastic image on one display screen in an overlapping manner. Alternatively, two screens of a monochrome tomographic image and a monochrome elastic image may be simultaneously displayed on the same screen. The monochrome tomographic image is not particularly limited to an ordinary B image. A tissue harmonic tomographic image may be used which is an image generated by selecting the harmonic content of a reception signal. Similarly a tissue Doppler image may be displayed instead of the monochrome tomographic image. Additionally, images to be displayed on dual screens may be selected from various combinations.

Regarding the formation of the elastic image, the above explanation described the case where elastic image data is generated after a distortion or a Young's modulus $Y_m$ of living tissue is obtained. The present invention is not limited to this case. For example, an elastic modulus may be calculated using other parameters such as a stiffness parameter β, a pressure elastic modulus $E_p$, and an incremental elastic modulus $E_{inc}$ (see JP-A-5-317313).

The embodiment shown in FIG. 1 described the case where an ultrasound probe is brought into contact with the body surface of a test subject. The present invention is not limited to this case. A transoesophageal probe or an intravascular probe may be similarly used. According to this embodiment, it is possible to achieve high reliability and stability in the ultrasonographic device.

According to this invention, it is possible to stably visualize an elastic image with a high resolution at a given time and simultaneously achieve means for visualizing, as an image sequence, the response of palpation conventionally conducted by the doctor, thereby providing an ultrasonographic device which is clinically useful while keeping the real-time performance and convenience of ultrasonography.

Having described examples of the present invention. It will be obvious to those skilled in the art that the present invention is not limited to these examples and various modifications and variations are possible within the spirit of the present invention and the scope of the appended claims.

The invention claimed is:

1. An ultrasonographic device, comprising:
   an ultrasound prove including an oscillator for generating an ultrasonic wave;
   an ultrasonic wave transmitter/receiver circuit which is connected to the probe and transmits and receives the ultrasonic wave to and from a test subject;
   a phasing addition circuit which controls a phase of the received ultrasonic wave and generates RF signal frame data;
   a memory for storing a plurality of said RF signal frame data;
   a RF signal frame data selection section for selecting latest RF signal frame data and past RF signal frame data from said memory with a variable frame interval;
   an elastic frame data calculation section for generating elastic frame data in time sequence based on a pair of the RF signal frame data, the elastic frame data indicating a distortion or an elastic modulus of each point on a tomographic image; and
   an elastic image generating section for generating an elastic image based on the elastic frame data,
   wherein said elastic image generating section includes:
      a statistical processing circuit for performing statistical processing on the two or more elastic frame data corresponding to a target processing area and obtaining a statistical characteristic amount,
      circuitry for setting an upper limit value and a lower limit value for imaging the elastic frame data, for each of the elastic frame data based on the statistical characteristic amount,
      circuitry for generating elastic image data from the elastic frame data while matching the upper limit value and the lower limit value with a range of the predetermined display gradation, and
      a frame interval optimization circuit which receives, from the RF signal frame data selection section, the number of frame intervals between a pair of RF signal frame data used for generating elastic frame data for a current image configuration, and calculates an optimum number of frame intervals of a pair of RF signal frame data to be used for generating elastic frame data for a subsequent image configuration, based on the inputted number of frame intervals and the statistical characteristic amount, and
   wherein the RF signal frame data selection section includes a RF signal frame data selection circuit, which is connected to the frame interval optimization circuit, for determining the number of frame intervals of the pair of RF signal frame data to be used for generating elastic frame data for a subsequent image configuration, based on the optimum number of frame intervals inputted from the frame interval optimization circuit.

2. The ultrasonographic device according to claim 1, wherein the frame interval optimization circuit includes:
   circuitry for calculating the optimum number of frame intervals based on the inputted number of fame intervals and average value of distortion amounts.

* * * * *